US006670455B1

(12) United States Patent
Roemisch et al.

(10) Patent No.: US 6,670,455 B1
(45) Date of Patent: *Dec. 30, 2003

(54) PROCESS FOR THE PREPARATION IN PURE FORM OF THE PROTEASE ACTIVATING BLOOD CLOTTING VII, ITS PROENZYME OR A MIXTURE OF BOTH PROTEINS BY MEANS OF AFFINITY CHROMATOGRAPHY

(75) Inventors: Juergen Roemisch, Marburg (DE); Annette Feussner, Marburg (DE); Hans-Arnold Stoehr, Wetter (DE)

(73) Assignee: Aventis Behring GmbH, Marburg (DE)

( * ) Notice: Subject to any disclaimer, the term of this patent is extended or adjusted under 35 U.S.C. 154(b) by 135 days.

This patent is subject to a terminal disclaimer.

(21) Appl. No.: 09/632,974

(22) Filed: Aug. 4, 2000

(30) Foreign Application Priority Data

Aug. 6, 1999 (DE) .......................... 199 37 218

(51) Int. Cl.$^7$ .......................... A61K 35/14; C07K 1/00; C07K 1/16
(52) U.S. Cl. .................. 530/412; 530/381; 530/300; 530/350; 514/2; 435/69.2; 435/69.6
(58) Field of Search ................ 530/412, 381, 530/300, 350; 424/400; 604/19; 435/69.2, 69.6; 514/2

(56) References Cited

U.S. PATENT DOCUMENTS

| | | | |
|---|---|---|---|
| 3,717,708 A | 2/1973 | Wada et al. | 424/177 |
| 5,344,918 A | 9/1994 | Dazey et al. | 530/381 |
| 5,679,776 A | 10/1997 | Burnouf-Radosevich et al. | 530/383 |

FOREIGN PATENT DOCUMENTS

| | | |
|---|---|---|
| DE | 199 26 531.3 | 6/1999 |
| DE | 199 03 693.4 | 10/1999 |

OTHER PUBLICATIONS

"Proteolytic Enzymes" p. 327, (1989) Edited by Benyon, R and Bond, J. S., Oxford University Press, Oxford.*
Scopes, R. K. (1987) "Protein Purification" p. 126–127, second edition, Springer–Verlag, New York et al.*

Choi–Miura, N., et al., Purification and Characterization of a Novel Hyaluronan–Binding Protein (PHBP) from Human Plasma: It Has Three EGF, a Kringle and a Serine Protease Domain, Similar to Hepatocyte Growth Factor Activator, J. Biochem., vol. 119, pp. 1157–1165 (1996).

Hashimoto, K., et al., Cloning of the cDNA for a Mouse Homologue of Human PHBP: a Novel Hyaluronan–Binding Protein, Biol. Pharm. Bulletin, vol. 20, No. 11, pp. 1127–1130 (1997).

Sumiya, J., et al., Isolation and Characterization of the Plasma Hyaluronan–Binding Protein (PHBP) Gene (HABP2), J. Biochem., vol. 122, pp. 983–990 (1997).

Vostrov, A., et al., Plasma Hyaluronan–binding Protein Is a Serine Protease, J. Biological Chemistry, vol. 275, No. 30, pp. 22978–22985 (Jul. 2000).

Choi–Miura, N., et al., *Purification and Characterization of a Novel Hyaluronan–Binding Protein (PHBP) from Human Plasma: It has Three EGF, a Kringle and a Serine Protease Domain, Similar to Hepatocyte Growth Factor Activator*, J. Biochem., vol. 119, pp. 1157–1165 (1996).

* cited by examiner

Primary Examiner—Karen Cochrane Carlson
Assistant Examiner—Samuel W. Liu
(74) Attorney, Agent, or Firm—Finnegan, Henderson, Farabow, Garrett and Dunner, L.L.P.

(57) ABSTRACT

A process for the preparation in pure form of the protease activating blood clotting factor VII and/or its proenzyme by the use of a chromatography separation processes and/or fractional precipitation is described. The process used may include adsorption on calcium phosphate/hydroxyapatite, a hydrophobic matrix, a chelate matrix, a matrix on which heparin or a substance related to heparin, such as heparin sulfate or dextran sulfate, is immobilized, or a matrix that is coated with an immobilized monoclonal or polyclonal antibody directed against the protein to be isolated, or F(ab) or F(ab)$_2$ fragments of antibodies directed against the protein to be isolated. A pharmaceutical preparation and a reagent are described which contain the said protease and/or its proenzyme.

13 Claims, No Drawings

PROCESS FOR THE PREPARATION IN PURE FORM OF THE PROTEASE ACTIVATING BLOOD CLOTTING VII, ITS PROENZYME OR A MIXTURE OF BOTH PROTEINS BY MEANS OF AFFINITY CHROMATOGRAPHY

The invention relates to a process for the preparation in pure form of the protease activating blood clotting factor VII, its proenzyme or a mixture of both proteins, and of pharmaceutical preparations which contain the proteins mentioned individually or as a mixture.

German patent application 19 903 693.4 has already disclosed a protease for the activation of blood clotting factor VII, a process for its production, for its detection and for its inactivation, and pharmaceutical preparations which contain this protease. This protease, first isolated from plasma, occurs there together with a nonactivated form, which is designated below as "proenzyme". The protease activates blood clotting factor VII and accelerates clotting, as was shown by numerous experiments. In the further investigation of the biological properties of this protein, identified as serine protease, it emerged that single-chain plasminogen activators, such as prourokinase, are also effectively activated. Moreover, inactivation of factors V and VIII in vitro was observed. In addition to the sequenced regions already described in German patent application 19 903 693.4, N-terminal sequencings of protease fractions were carried out. The following amino acid sequences characterize the FVII-activating protease: IYGGFKSTAGKHP; LLE-SLDPDXTPD; EFHEQSFRVEKI; SKFTXAXPXQFK; where X means not identified. The sequences of the protease mentioned elucidated up to now show that they agree 100% with sequences of the protease published by Choi-Miura (Choi-Miura et al. J. Biochem. 1996; 119: 1157 to 1165).

The investigations until now have especially concentrated on the protease in its activated form. The inactive form of the protease present in the plasma as a proenzyme was only recently discovered by means of a protein band pattern in the SDS-PAGE after reduction of the sample. Since, on the activation of the protease, a cleavage at a site of the primary structure typical for serine proteases and thus activation takes place, two or more bands are visible on electrophoresis. On reduction of the chains which are connected by disulfide bridges, the individual bands become visible in accordance with their lower molecular weight, the proenzyme remaining as a large individual chain. This was also clear in more complex solutions after transfer of the proteins to membranes and subsequent Western blotting using suitable antibodies.

For therapeutic reasons, there is now an interest in having available both the protease in its activated form and the proenzyme, in addition to the mixture of the two proteins mentioned. Whereas the activated protease can be used for the rapid activation of blood clotting factor VII or the single-chain plasminogen activators in order to influence acute syndromes, the proenzyme form of the protease is especially to be chosen as a preferred agent for medium- to longer-term prophylaxis or treatment of inherited or acquired deficiency states or alternatively for increasing the plasma level beyond the physiological extent. However, it is to be taken into account here that the stabilization of an activated protease is difficult, since, for example, self-degradation can take place or the molecule can be unstable on account of its structural conditions. Previous studies showed that the protease activating factor VII can only be isolated and stabilized in its proenzyme form under special circumstances.

The investigations until now have shown that the biological activities of this protease can be increased by calcium and/or heparin or substances related to this. This property has already been previously used in order to adsorb the protease on immobilized heparin and to obtain an enriched fraction. Moreover, it is already known that anion-exchange chromatography is also suitable for the purification of the protease. The combination of both purification steps is suitable for obtaining the protease in enriched form. An aprotinin matrix can also be used for the preparation in pure form of the activated protease.

A process for the preparation in pure form of the protease activating blood clotting factor VII and/or its proenzyme has now been found, in which one or more affinity chromatography separation processes and/or fractional precipitation are employed.

Affinity chromatography separation processes which can be used are adsorption on calcium phosphate/hydroxyapatite,
a hydrophobic matrix,
a chelate matrix,
a matrix on which heparin or a substance related to heparin, such as heparan sulfate or dextran sulfate, is immobilized, and/or a matrix which is coated with an immobilized monoclonal or polyclonal antibody directed against the protein to be isolated, or its F(ab) or F(ab)$_2$ fragments.

A simple and rapid method for the enrichment of the protease and of the proenzyme is in this case adsorption on calcium phosphate/hydroxyapatite. In the course of this, the solution which contains the protease and the proenzyme is mixed with calcium phosphate at a pH of between 2.5 and 9.0, preferably between 2.5 and approximately 7.2. After subsequent sedimentation, e.g. by centrifugation or by filtration, the sediment, optionally after resuspending one or more times in a buffer solution, is eluted with addition of, for example, 0.2 M sodium citrate. The protease and the proenzyme are then found in the eluate.

The adsorption of the protease on hydrophobic matrices or on hydrophobic ligands which are coupled to appropriate matrices can also be used according to the invention. Examples are phenyl- and octyl-sepharoses or a phenylalanine coupled to a matrix. The bound protein is eluted in a manner known per se using a buffered solution of low ionic strength, which can contain phenylalanine, glycerol or ethylene glycol.

Since the protease and the proenzyme enter into an interaction with cations, especially with calcium and magnesium ions, which is confirmed by an increase in their activity in the presence thereof, chromatography by means of so-called "chelate matrices" suggests itself for enrichment thereof from corresponding solutions. Chelate compounds with zinc, copper or nickel ions are particularly suitable here. After the washing of the matrix loaded with the protease, an imidazole buffer, if appropriate with a linear gradient, can also be employed for the elution of bound proteins.

The process according to the invention can also be carried out by removing the said proteins by fractional precipitation, e.g. by addition of polyethylene glycol or ammonium sulfate, from the liquids containing them. Fractional precipitations of this type can be employed as the sole separation process, but the yield and the effectiveness of the process according to the invention are further improved if it is combined in any desired sequence with other purification processes known per se. It is thus possible, by admixture of polyethylene glycol (preferably PEG 6000) from 10% final concentration to a solution containing the protease activating factor VII and the proenzyme in the pH range from 2.5 to 9.0, to carry out a precipitation of the protease and of the proenzyme without a loss of activity occurring in the course of this. Owing to fractional PEG precipitation which is achievable thereby, separation of impurities is possible. This also applies to fractional precipitation by means of ammonium sulfate, from approximately 15% final concentration. The protease precipitates obtained can not only be stored without loss of activity, they are particularly suitable for the concentration of the protease and of the proenzyme, so that the preparation in pure form of the proteins mentioned is possible in a shorter time and, moreover, exposure of the protease to activating surfaces which lead to losses of activity, such as occurs, for example, in the use of filters, is avoided.

In general, however, it is expedient to carry out all process steps for the isolation of the protease and of the corresponding proenzyme from a solution containing these proteins, such as plasma, plasma fractions, tissue fluids or cell culture supernatants of the recombinantly or transgenically expressed protease or mutants thereof in the presence of protein stabilizers. The same also applies to the storage of the proteins mentioned and their use in pharmaceutical preparations. Particularly expediently, a combination of a number of protein stabilizers can be used, where the protein stabilizers should be selected from the following substance groups:

- complexing agents of divalent ions, preferably ethylenediaminetetraacetic acid (EDTA), [ethylenebis(oxyethylenenitrilo)]tetraacetic acid (EGTA), or citrate, and/or
- divalent ions, preferably calcium ions, and/or
- amino acids, preferably glutamate, arginine, lysine or glycine, and/or
- sugars, preferably glucose, arabinose, mannose or mannitol, and/or
- solubilizers, preferably hydroxyproline, and/or
- detergents, preferably a polyoxyethylenesorbitan fatty acid ester (Tween®) or an octylphenoxypolyoxyethanol (Triton®), and/or
- alcohols, preferably ethylene glycol or polyethylene glycol, and/or
- proteins, preferably albumin, gelatin, fibronectin, vitronectin or similar proteins, and/or
- reductants, preferably dithiothreitol, mercaptoethanol or cysteine, and/or
- proteinase inhibitors such as aprotinin, $\alpha_2$-antiplasmin, C1-esterase inhibitor, the inter-$\alpha$-trypsin inhibitor, the antithrombin III/heparin inhibitor or synthetic inhibitors.

It is particularly worthy of note that in the processes described above the proenzyme form of the protease can also be obtained in pure form. As a matter of fact, it was seen that it was possible under the said acidic conditions to obtain, from a solution containing the proenzyme, an eluate which contained the proenzyme exclusively or at least to a very greatly enriched extent. In this case, the nativity of the proenzyme thus obtained can be determined with the aid of one of the activity tests which are described in German patent application 196 26 531.3. i.e., for example, by the photometric determination of the extinction occurring in the case of action on chromogenic substrates or by the single-chain formation occurring after reduction of the sample, which can be detected by SDS-PAGE/Western blotting. This shows that according to the invention the preparation of the proenzyme is possible in a rapid and efficient manner and with a high yield.

When using the above mentioned process steps, it is thus possible to obtain both the purified protease activating factor VII, its proenzyme or, alternatively, a mixture of the activated protease and the proenzyme. A route which is particularly worthy of mention for the preparation of a pure activated protease consists in the chromatographic separation of the protease activating factor VII from its proenzyme by means of stepwise elution, in which a substance which has bonds of different strength to the protease on the one hand and to the proenzyme on the other hand is immobilized on the support material. Different eluates can thus be obtained which contain either only the activated protease or only the proenzyme.

Therapeutically, the said activated protease, the proenzyme or the mixture of both compounds can be used to assist blood clotting in the case of a tendency to bleeding, in the case of absence of factors of the endogenous clotting branch or as FEIBA (=factor VIII bypassing activity), but also for the endogenous and exogenous activation of plasminogen activators such as prourokinase or single-chain tPA. This activity can also be employed in combination with single-chain or double-chain plasminogen activators or anticoagulants by use of the said protease for the prophylaxis or therapy of thromboembolic disorders. Syndromes which are associated with thrombotic complications, such as cardiac infarct, angina pectoris, stroke or leg vein thromboses, can thus be successfully treated.

A further subject of the invention is therefore a pharmaceutical preparation which contains an amount of the protease activating blood clotting factor VII and/or its proenzyme form sufficient for the dissolution of fibrin-containing thrombi. This preparation can also moreover contain single-chain plasminogen activators and/or anticoagulants. Expediently, a proteinase stabilizer or a reductant such as dithiothreitol, mercaptoethanol or cysteine is additionally added to the preparation in order to reduce the risk of polymer formation during processing or on storage.

Fibrinolytic processes also play a part in wound-healing processes. In this case, the said protease and/or the proenzyme can be administered intravenously or locally, subcutaneously, intradermally, intramuscularly or, in the case of injuries and wounds, as a constituent of a fibrin adhesive or alternatively topically or bound to a suitable carrier matrix, e.g. in the form of a web or of a patch, where combination with growth factors can be expedient. In general, a pharmaceutical preparation of this type is used in liquid or lyophilized form, to which protein stabilizers known per se can be added, i.e., for example, complexing agents, divalent cations such as calcium, amino acids such as glutamate, arginine, lysine or glycine and/or sugars such as glucose, arabinose, mannose or mannitol.

Moreover, the protease and/or its proenzyme can also be employed for the coating of articles consisting of plastics or metals to be implanted in the body, such as synthetic heart valves, blood vessels, but also cannulas inserted for taking blood or artificial feeding.

The invention is illustrated by the following examples:

EXAMPLE 1

Preparation in Pure Form by Means of Immobilized Monoclonal Antibodies

Monoclonal antibodies which are directed against the protease activating factor VII were coupled to BrCNsepharose. 30 ml of this mAb matrix were packed into a column and the resin was equilibrated with 50 mM sodium citrate, 0.1 M sodium chloride (NaCl), 0.1 M arginine×HCL, pH 6.0.

100 ml of citrate plasma were pumped through the column and the matrix was then washed with 50 mM sodium citrate, 1 M NaCl, 0.1 M arginine×HCl, pH 6.0. The column was then washed again with the equilibration buffer, after which elution with 0.1 M glycine, pH 2.5, followed. The eluate (about 30 ml) was collected in a volume of 3 ml of 200 mM sodium citrate solution, pH 5.5, with stirring and then adjusted to a pH of 4.5.

The eluate solution was used for further analysis. An SDS-PAGE with subsequent transfer to a PVDF membrane and detection of the factor VII activator band was carried out using the unreduced and using the reduced sample. Activity tests of the proteins thus obtained were carried out according to the process described in German patent application 199 26 531.3, namely the activation of prourokinase and factor VII, with subsequent detection of urokinase or activated factor VII. The amounts of protease tested in this system, determined as protease antigen, correspond to the expected theoretical activity, whereby the activity of the isolated protease or of the proenzyme with respect to the biological activity was shown.

EXAMPLE 2

Anion-exchange Chromatography

A solution containing the proenzyme form of the factor VII-activating protease and which still contained contaminations by other proteins was pumped onto Mono Q sepharose in a buffer solution of 20 mM Na acetate, 0.1 M glycine, pH 4.5 and then washed with the abovementioned buffer. The fraction passing through was collected. Bound proteins were eluted using 20 mM Na acetate, 2 M NaCl, pH 4.5. The elute was diluted in a buffer of 5 mM Na citrate, 50 mM NaCl, pH 6.0, and investigated in the test systems mentioned in Example 1. Aliquots were stored at 4 to 8° C. or frozen at −20° C.

After storage of the eluate solution at 6° C. for several days, the tests were repeated, the dilutions of the (thawed) samples in each case being carried out shortly before the test.

SDS-PAGEs/Western blots confirmed that the protease had been isolated in its proenzyme form. After SDS-PAGE and staining of proteins by means of Coomassie Blue, in addition to the protease a number of contaminating proteins, which were also to be found in the fractions passing through, were visible in the starting solution (before chromatography). The protease was represented as a band corresponding to the proenzyme form (i.e. even after reduction) in pure form. The activity tests (see Example 1) confirmed the nativity of the protease in the sense of the retention of the biological activities.

What is claimed is:

1. A process for the preparation of a protein wherein the protein is the pure form of the protease activating blood clotting factor VII, the pure form of a proenzyme for the protease, or a mixture of both the pure form of the protease and the pure form of the proenzyme, and wherein the protein is purified by a chromatography separation process, a fractional precipitation, or a combination of both a chromatography process and a fractional precipitation, and wherein during said chromatography separation process, the protein is absorbed on one of:

a) calcium phosphate/hydroxyapatite
b) a hydrophobic matrix;
c) a chelate matrix
d) a matrix on which heparin or a substance related to heparin is immobilized, or
e) a matrix which is coated with an immobilized monoclonal or polyclonal antibody directed against the protein to be isolated, or F(ab) or F(ab)$_2$ fragments of antibodies directed against the protein to be isolated.

2. The process according to claim 1, wherein the substance related to heparin is heparin sulfate or dextran sulfate.

3. The process according to claim 1, wherein the protein is absorbed on calcium phosphate/hydroxyapatite, wherein:

a) a solution which contains the protein is mixed with calcium phosphate at a pH of between 2.5 and 9.0;
b) the protein is collected by sedimentation;
c) the sediment is resuspended one or more times in a buffer solution;
d) the protein is eluted; and
e) the protein is found in the eluate.

4. The process according to claim 1, wherein the protein is absorbed on a hydrophobic matrix, wherein:

hydrophobic ligands are coupled to the hydrophobic matrix; and
the absorbed protein is eluted in a buffered solution of low ionic strength.

5. The process according to claim 4, wherein the hydrophobic ligands are the phenyl derivative of aliphatic hydrophobic agarose beads, the octyl derivative of aliphatic hydrophobic agarose beads, or phenylalamine.

6. The process according to claim 1, wherein the protein is absorbed on a chelate matrix, wherein:

a) the chelate matrix comprises chelate compounds comprising ions chosen from the group consisting of zinc, copper, and nickel ions in any ionization state; and
b) after washing the matrix loaded with the protein, a buffer is used to elute the protein.

7. The process according to claim 1, wherein the fractional precipitation of the protein from its solution is carried out by addition of:

a) polyethylene glycol from a concentration of at least 10% by weight, or
b) ammonium sulfate from a concentration of at least 15% by weight.

8. The process according to claim 1, wherein protease activating blood clotting factor VII is separated from its proenzyme by chromatography separation, wherein:

a) a substance having different binding strength to the protease and proenzyme is immobilized on a support material;
b) the proteins are eluted sequentially;
c) the different eluates are collected separately from one another; and
d) the respective protease or proenzyme is obtained from the eluate.

9. The process according to claim 8, wherein an acidic solution is used to elute only the proenzyme.

10. The process according to any one of claims 1–4 and 6–8, which is carried out in the presence of one or more protein stabilizers selected from the group consisting of a) complexing agents of divalent ions;
b) divalent ions;
c) amino acids;

d) sugars;

e) solubilizers;

f) detergents;

g) alcohols;

h) proteins;

i) reductants; and j) protease inhibitors.

11. The process according to any one of claims 1–4 and 6–8, wherein the protein is isolated from a solution, and wherein the solution is plasma, plasma fractions, tissue fluids, or cell culture supernatants of recombinantly or transgenically expressed proteins, protein proenzymes, or mutant proteins or proenzymes.

12. The process according to claim 10, wherein:

a) the complexing agent of divalent ions is ethylenediaminetetraacetic acid, ethylenebis(oxyethylenenotrilo) tetraacetic acid, or citrate;

b) the divalent ions are calcium ions;

c) the amino acids are glutamate, arginine, lysine, or glysine;

d) the sugar is glucose, arabinose, mannose, or mannitol;

e) the solubilizer is hydroxyproline;

f) the detergent is a polyoxyethylenesorbitan fatty acid ester or a octylphenoxypolyoxyethanol;

g) the alcohol is ethylene glycol or polyethylene glycol;

h) the protein is albumin, gelatin, fibrobectin, vitronectin, or similar proteins;

i) the reductant is dithiothreitol, mercaptoethanol, or cysteine; and j) the protease inhibitor is aprotinin, $\alpha_2$-antiplasmin, C1-esterase inhibitor, inter-$\alpha$-trypsin inhibitor or antithrombin III/heparin inhibitor.

13. The process according to claim 10, wherein the protease inhibitors are synthetic inhibitors.

* * * * *

UNITED STATES PATENT AND TRADEMARK OFFICE
CERTIFICATE OF CORRECTION

PATENT NO. : 6,670,455 B1
DATED : December 30, 2003
INVENTOR(S) : Juergen Roemisch et al.

It is certified that error appears in the above-identified patent and that said Letters Patent is hereby corrected as shown below:

<u>Title page, Item [54] and Column 1, line 3,</u>
Title, after "BLOOD CLOTTING", insert -- FACTOR --.

Signed and Sealed this

Fourth Day of January, 2005

JON W. DUDAS
*Director of the United States Patent and Trademark Office*